US005520892A

United States Patent [19]
Bowen

[11] Patent Number: 5,520,892
[45] Date of Patent: May 28, 1996

[54] STERILIZATION UNIT FOR DENTAL HANDPIECES AND OTHER INSTRUMENTS

[76] Inventor: John G. Bowen, 132 Dyer Rd., Santa Ana, Calif. 92707

[21] Appl. No.: 225,806

[22] Filed: Apr. 11, 1994

[51] Int. Cl.$^6$ .................... A61L 2/06; A61L 2/20
[52] U.S. Cl. .................... 422/295; 422/297; 422/300
[58] Field of Search .................... 422/26, 27, 28, 422/38, 109, 112, 116, 295–7, 298, 299, 292, 300, 307; 219/521, 385, 386; 165/58

[56] References Cited

U.S. PATENT DOCUMENTS

| | | | |
|---|---|---|---|
| 3,848,336 | 11/1974 | Copeland | 433/99 |
| 4,027,727 | 6/1977 | Pullens | 165/58 |
| 4,327,060 | 4/1982 | Nisii | 422/300 |
| 4,376,096 | 3/1983 | Bowen | 422/307 |
| 4,400,357 | 8/1983 | Hohmann | 422/300 |
| 4,529,868 | 7/1985 | Bowen et al. | 422/38 |
| 4,590,037 | 5/1986 | Kaye | 422/116 |
| 4,710,350 | 12/1987 | Petersen | 422/295 |
| 4,892,706 | 1/1990 | Kralovic et al. | 422/28 |
| 5,137,689 | 8/1992 | Cantrell | 422/300 |
| 5,256,382 | 10/1993 | Ford et al. | 422/298 |
| 5,290,511 | 3/1994 | Newmah | 422/26 |
| 5,348,678 | 9/1994 | Hodam, Jr. et al. | 252/106 |

*Primary Examiner*—Robert J. Warden
*Assistant Examiner*—Robert Carpenter
*Attorney, Agent, or Firm*—Keith D. Beecher

[57] ABSTRACT

A sterilization unit for dental handpieces and other instruments, and which finds utility in the sterilization of any surgical instrument, or the like, which breaks the skin or comes into contact with body fluids, and which are too delicate or have sharp edges which could become damaged in conventional present day autoclaves. The sterilization unit of the present invention combines heat, steam pressure and time in a precisely controlled manner so that the handpieces, or other surgical instruments are not damaged during the sterilization procedure. This is achieved by providing a total cycle time including cooling to a patient-ready condition of less than 20 minutes. A unique control system places the sterilizing chamber at a temperature which creates steam and pressure in a time frame that sterilizes the handpiece without damage to the turbine. Mineral-free water is flushed through the piping and turbine to clear out debris and insure sterilization and de-scaling of the inside as well as outside of each handpiece.

17 Claims, 9 Drawing Sheets

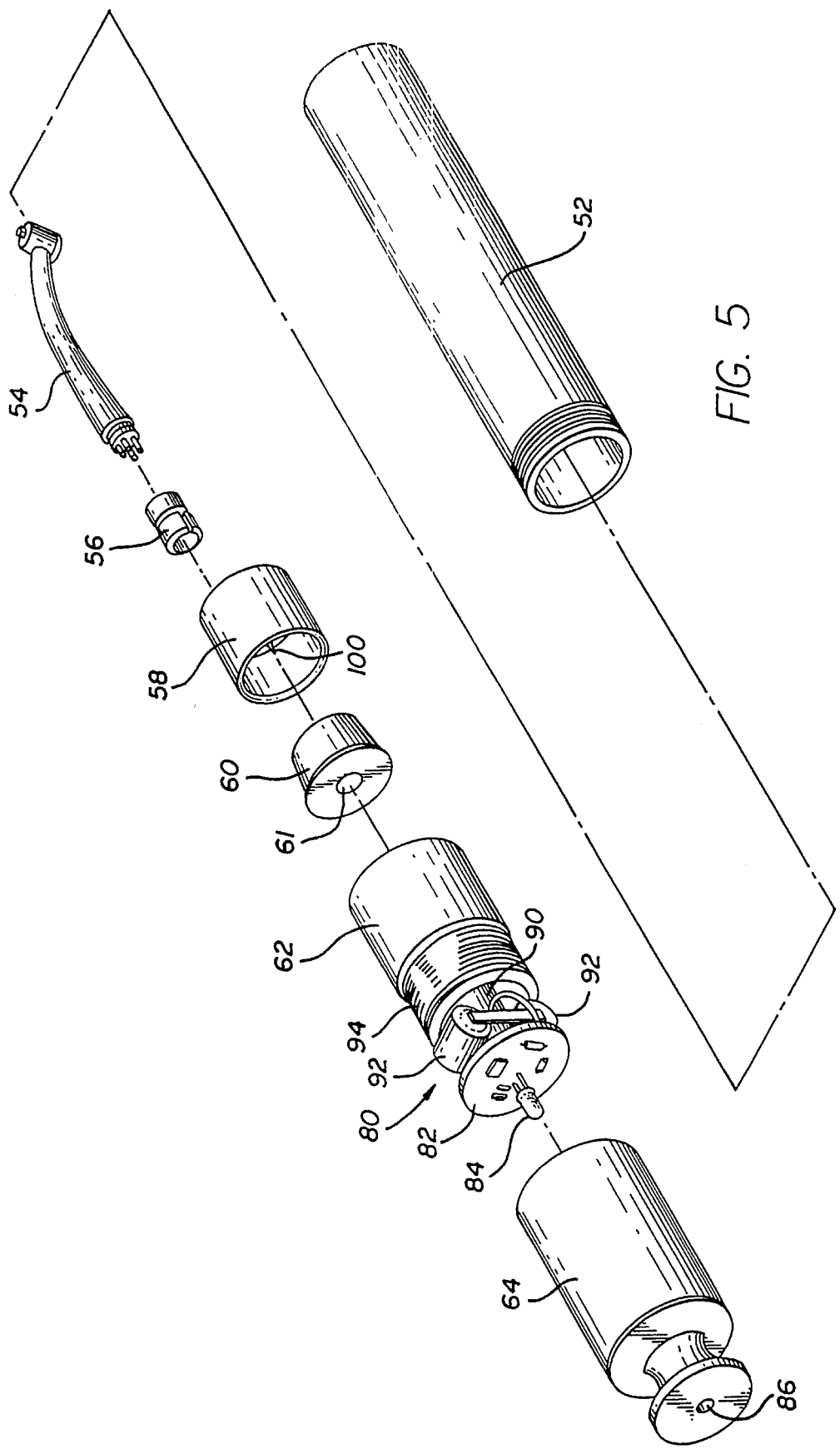

5,520,892

STERILIZATION UNIT FOR DENTAL HANDPIECES AND OTHER INSTRUMENTS

BACKGROUND OF THE INVENTION

The invention is concerned with a sterilization unit for dental handpieces and other instruments, such as endoscopes, proctoscopes, laprascopes, biopsy probes, scalpels, acupuncture needles, manicurist's instruments, tatoo artist's needles, and, in general, any instrument which when used breaks the skin of a patient, or comes in contact with body fluids. The unit of the invention is of the same general type described and claimed in U.S. Pat. No. 4,376,096 which issued Mar. 8, 1993 in the name of the present inventor.

All surgical instruments should be sterile before they can be safely used in the treatment of patients. Failure to use sterile instruments exposes patients to the risk of infection which may impede their recovery or, at worst, cause death. In order to prevent patients from suffering infection following surgical procedures it is therefore of the utmost importance that all those processes which are designed to produce sterile instruments be carried out efficiently.

The sterilization unit of the present invention has particular utility in the sterilization of dental handpieces and, for that reason, it will be described in the following specification in conjunction with dental handpieces. However, it is to be understood, as explained above, that the unit of the invention has general utility for sterilizing a wide range of surgical and other instruments.

At present, dental handpieces are not being sterilized on a patient-to-patient basis or even on a daily or periodic basis, throughout the dental profession. However, five states have now mandated between-patient heat sterilization of dental handpieces, and more states are expected to follow.

It is well established that dental handpieces can spread infectious diseases from patient-to-patient, or from patient to the dentist, nurse or other assistants. During the use of a dental handpiece, the head and turbine of the handpiece become repositories for blood and flesh particles. This is caused by direct contact with the patient and by back pressure of the air lines during use. The handpiece should be water flushed after each use to remove such particles, and it also should be sterilized to kill any diseases carried by infected blood.

However, most present day heat sterilization techniques tend to damage the dental handpiece, and particularly tend to damage the high speed turbine located in the head of the handpiece. The most direct and effective sterilization procedure is steam/heat sterilization, this being recommended by the CDC, FDA and ADA because the combination of heat, steam pressure and time will kill any disease. However, conventional steam/heat sterilizers such as autoclaves and the like, generate temperatures sufficiently elevated to damage the handpiece turbine. Accordingly, dentists who are now heat sterilizing their handpieces between patients are currently paying a high price to protect their patients from cross-contamination because of handpiece repair costs. A second deterrent to the use of autoclaves is that the sterilization cycle is too long, which means that the handpieces cannot be sterilized in the average time between patient treatment (20–30 minutes).

Accordingly, it is an object of the present invention to provide a heat sterilizing unit for dental handpieces, and other surgical instruments, that does not damage the instruments, and which requires a total cycle time including cooling to a patient-ready condition of less than 20 minutes.

The unit of the invention includes a unique heat control system which places the sterilizing chamber at a temperature which creates steam and pressure in a time frame that sterilizes the handpiece without damaging the turbine. Mineral-free water is flushed through the piping and turbine of the handpiece to clear out debris and to insure sterilization inside as well as outside each handpiece. The sterilization system, in the particular embodiment to be described, is capable of sterilizing up to three handpieces at a time, thereby providing twelve sterilized handpieces each hour.

A further object of the invention is to provide such an improved sterilization unit in which both the sterilizing process and cooling process are performed in a single unit and in a relatively rapid time frame, so as to permit interpatient sterilizing of the handpieces.

BRIEF DESCRIPTION OF THE DRAWINGS

FIG. 1 a is a rear view of the unit of FIG. 1;

FIG. 5 is a perspective exploded view of the elongated cartridge, but taken from the opposite end of the cartridge;

DETAILED DESCRIPTION OF THE ILLUSTRATED EMBODIMENT OF THE INVENTION

Figure 1:
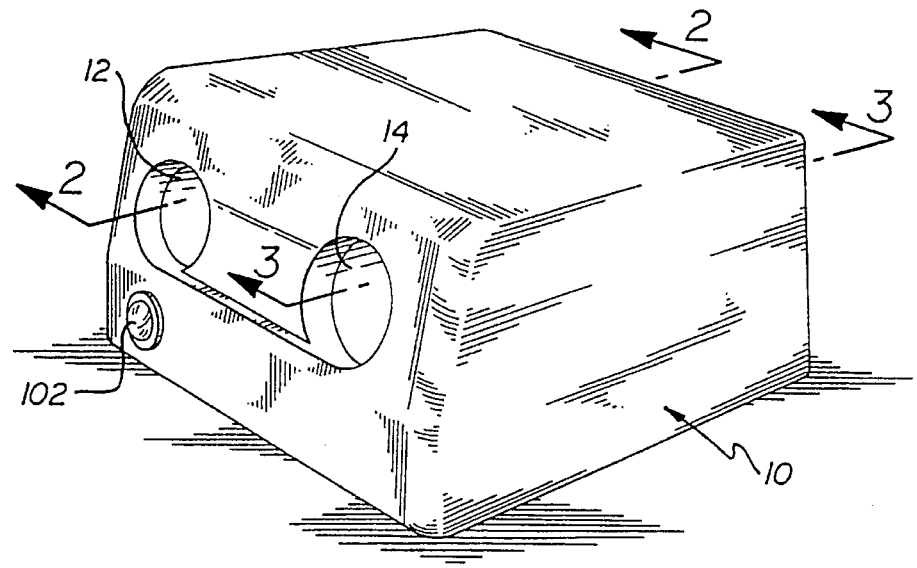
FIG. 1 is a perspective view of a sterilizing unit constructed in accordance with the concepts of the present invention and which includes a heating section and a cooling section into which an elongated cartridge, also constructed in accordance with the concepts of the invention, is successively inserted, the cartridge containing the handpiece, or other surgical instrument, to be sterilized.

As is mentioned above, the sterilizing unit constructed in accordance with one embodiment of the invention is shown in the perspective view of FIG. 1. The sterilizing unit is designated 10. It has two apertures 12 and 14 in its front face. The aperture 12 receives the elongated cartridge referred to above into the heating section of the sterilizing unit of FIG. 1, and the aperture 14 receives the elongated cartridge into the cooling section. To perform the sterilizing operation, the elongated cartridge is first inserted into the heating section through aperture 12, and then after a predetermined time, the cartridge is withdrawn from the heating section and inserted through aperture 14 into the cooling section for a second predetermined time. The cartridge is then removed, opened, and the sterilized handpiece, or other surgical instrument is removed.

Figure 2:
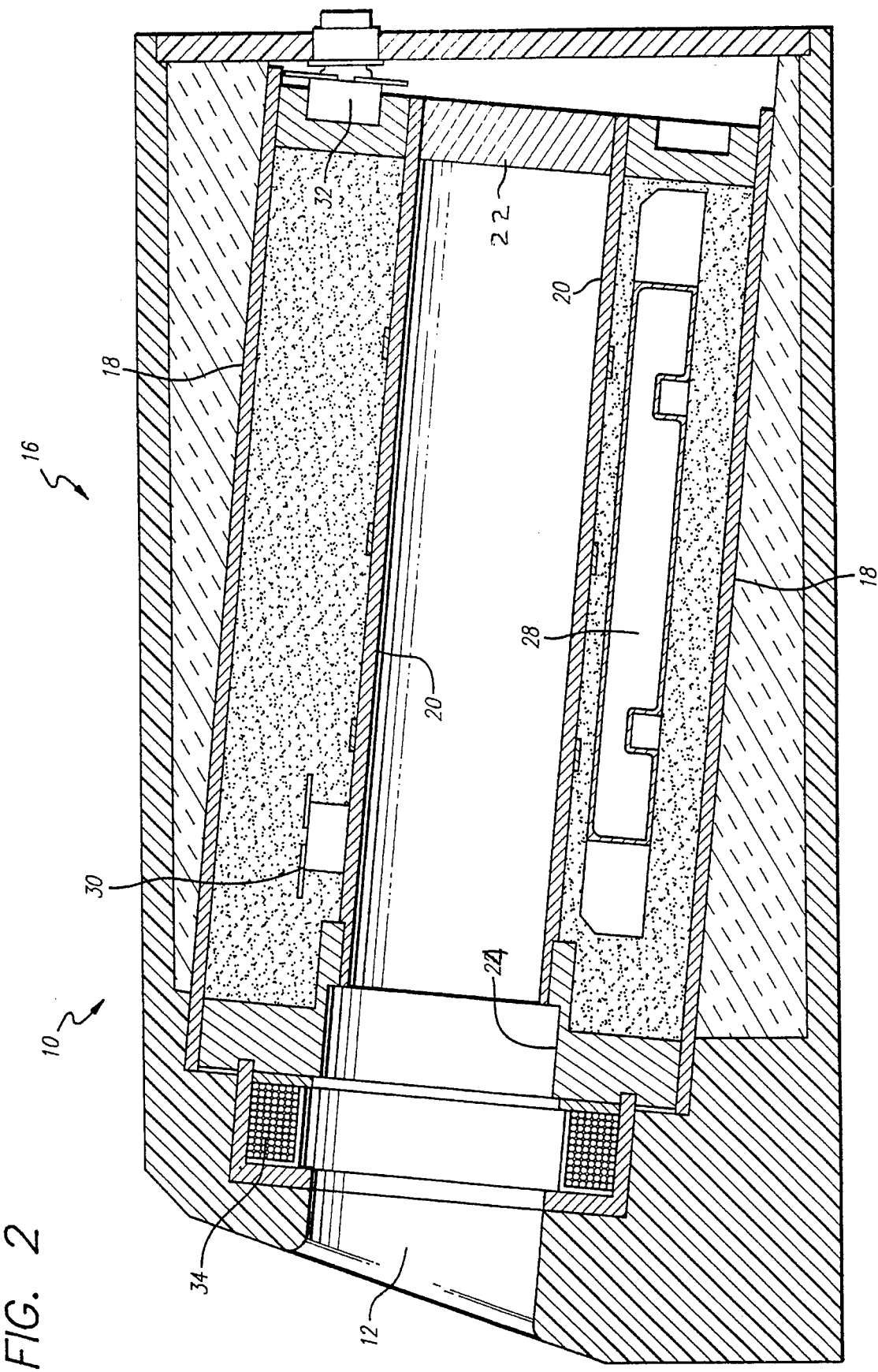
FIG. 2 is a sectional view taken along the lines 2—2 of FIG. 1 and showing the heating section of the sterilizing unit of FIG. 1.

The heating section of the sterilizing unit 10 of FIG. 1 is shown in the sectional view of FIG. 2, the heating section being designated as 16. As illustrated, the heating section includes an outer tubular aluminum case 18 and an inner tubular aluminum case 20 supported coaxially within the outer case. The aluminum cases 18 and 20 are held in an assembled condition by end walls 22 and 24, and the resulting structure is mounted within the sterilizing unit 10 coaxially disposed with respect to the aperture 12. The forward end wall 24 is of an annular form so that the elongated cartridge may be inserted through the aperture 12 and into the inner tubular case 20 in coaxial relationship therewith. The housing of unit 10 is formed of molded urethane, or other heat insulating material. The space between the wall of unit 10 and case 18 is filled with appropriate heat insulating foam.

An electric heater 28 is mounted within the annular space between the inner case 20 and outer case 18. A thermal switch 30 is also mounted in the annular space, as shown, and a second thermal switch 32 is mounted in the end wall 24 adjacent the end of the annular space. The annular space between the inner and outer tubular cases 18 and 20 is filled with paraffin which is sealed into the annular space, the electric heater 28 and switch 30 being immersed in the paraffin. An induction coil 34 is also mounted in the sterilizing unit to surround the aperture 12, as shown in FIG. 2. A steel magnetic core surrounds the induction coil 34 which also acts as a shield.

Figure 3:
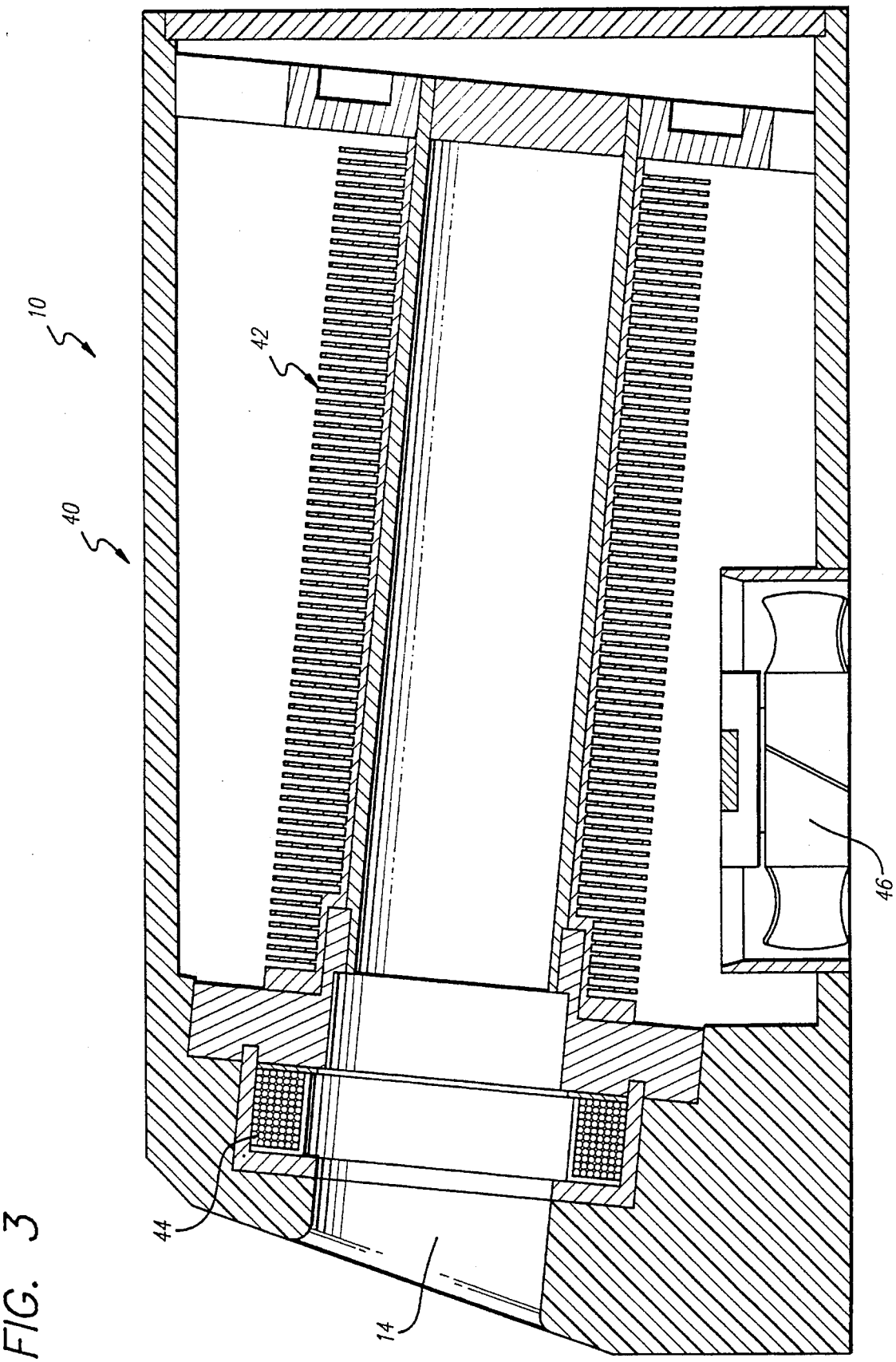
FIG. 3 is a sectional view taken along the lines 3—3 of FIG. 1 and showing the cooling section of the sterilizing unit of FIG. 1.

The cooling section of the sterilizing unit 10 of FIG. 1 is designated 40 in FIG. 3, and it includes a finned tube 42 mounted within the unit 10 in essentially coaxial relationship with the aperture 14. Tube 42 is suspended on the front and back of unit 10. An induction coil 44 surrounds the aperture 14, as shown, and it is surrounded by a magnetic core which also acts as a shield. A fan 46 is mounted in the wall of the unit 10 to set up a cooling flow of air around the finned tube rapidly to cool the cartridge when it is inserted into the finned tube.

A heat insulating panel (not shown) may be mounted in unit 10 between the heating and cooling sections. This panel may be formed, for example, of pressed glass.

Figure 6:
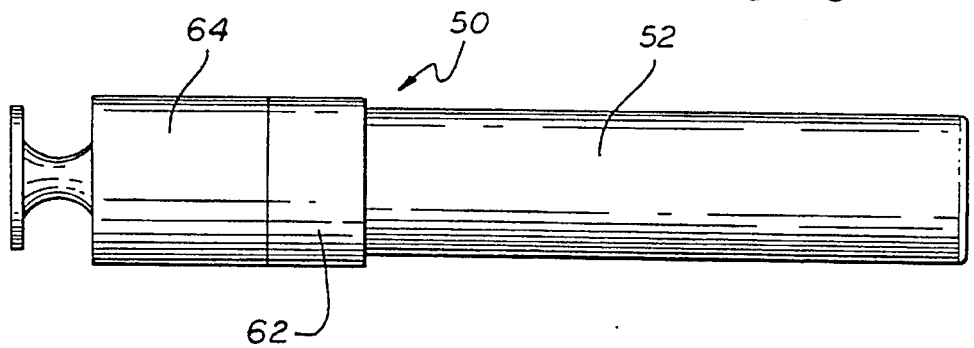
FIG. 6 shows the elongated cartridge in assembled form and ready to be inserted into the heating section 12 of the sterilizing unit of FIG. 1.
Figure 4:
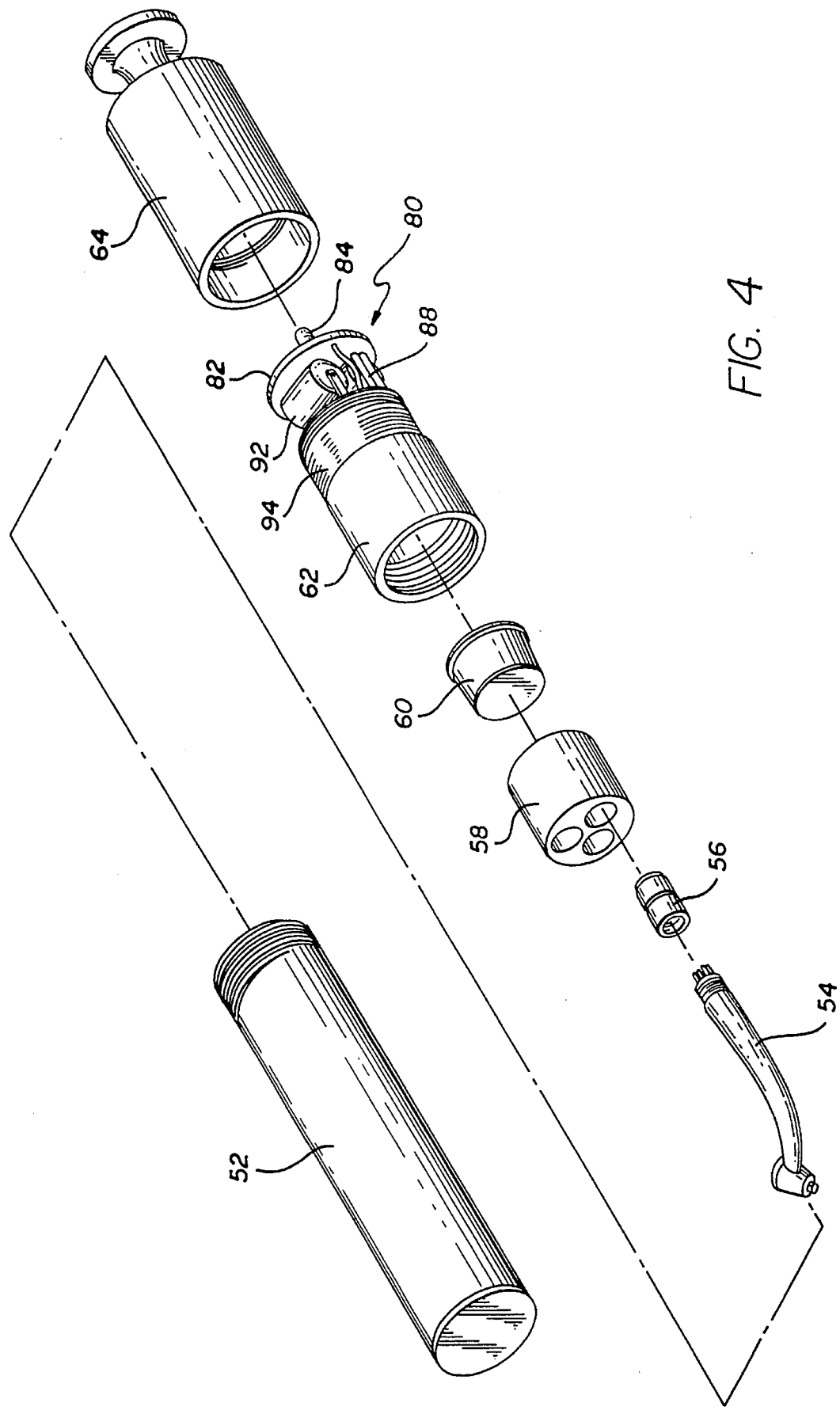
FIG. 4 is perspective exploded representation of the elongated cartridge which is inserted successively into the heating section and cooling section of the sterilizing unit of FIG. 1.

The elongated cartridge referred to above is designated 50 in FIGS. 4, 5 and 6. The cartridge 50, as shown in FIGS. 4, 5 and 6 includes a cylindrical housing 52 which is open at one end and closed at the other end. The housing 52 receives a handpiece 54, or other surgical instrument to be sterilized. The handpiece being inserted into the cylindrical housing 52 through its open end. A tubular adaptor 56 is threaded to one end of the handpiece 54, and it is received in a tubular insert 58 in a press fit with a channel in the insert. The insert, as best shown in FIG. 5 is constructed so that up to three handpieces 54 may be supported for simultaneous sterilizing. The insert 58 has a cup formed in its opposite end which receives a water ampoule 60. A cap 62 is fitted over the insert and threaded onto the end of the cylindrical housing 52. The cap 62 includes electronic circuitry, as will be described which performs a timing function. A cover 64 is fitted over the cap 62 and threaded onto the end of cap 62. A spring retainer is mounted in the end of cylindrical housing 52 to hold the insert 58 in place when the cover is threaded to the end of cap 62.

Figure 1A:
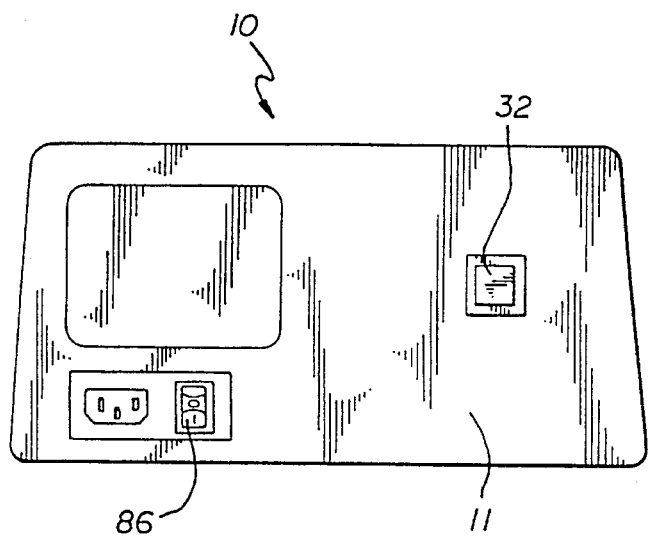
Figure 8:
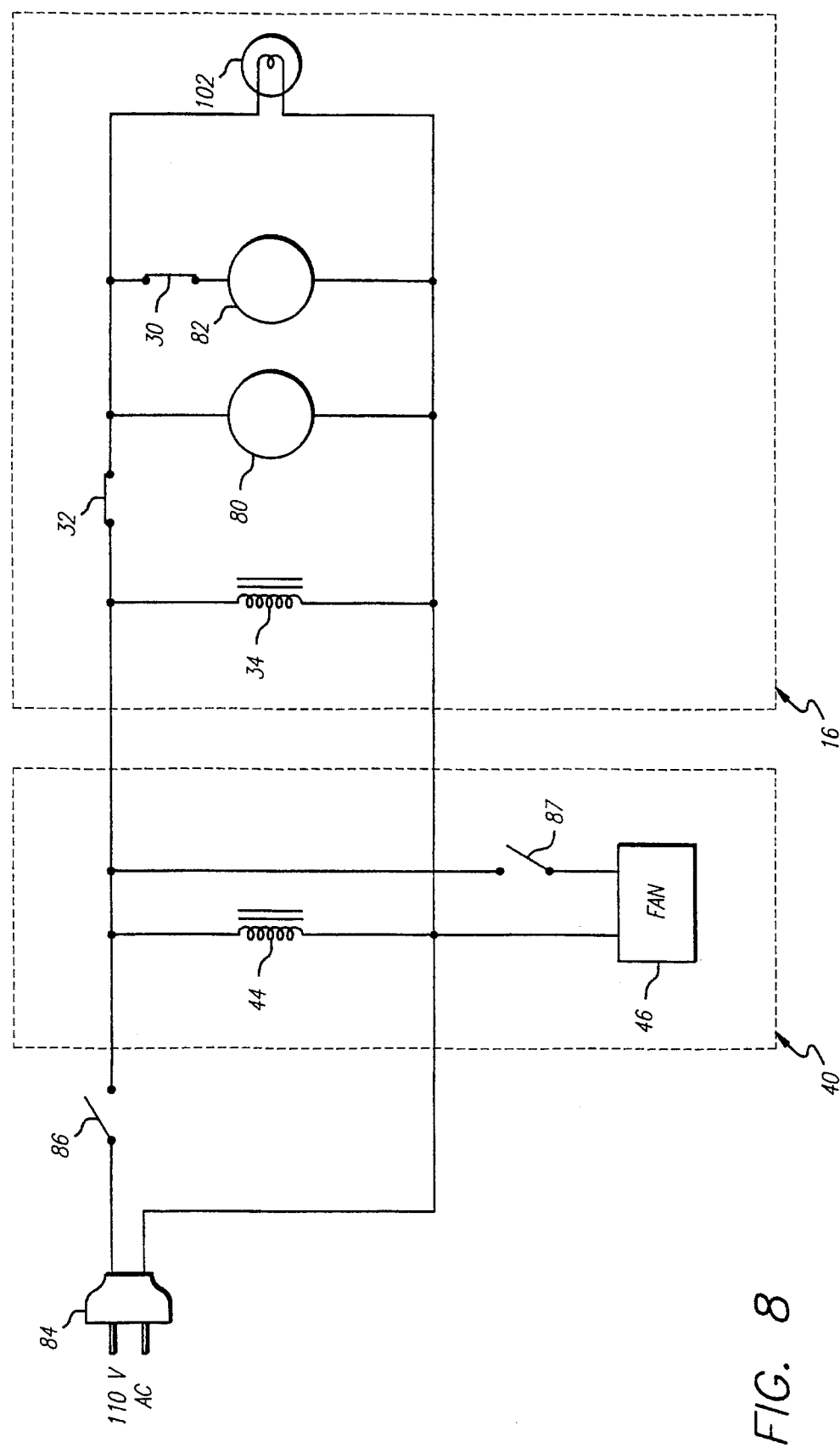
FIG. 8 is a circuit diagram showing how heating elements in heat up in the heating section of the sterilizing unit of FIG. 1 are energized and cool down in the cooling section.

As shown in the circuit diagram of FIG. 8, the electric heater 28 of FIG. 2 includes two Positive Temperature Coefficient (PTC) heating elements 80 and 82. The PTC heating element 80 is selected to have a Curie point of 150° C., and the heating element 82 is selected to have a Curie point of 190° C. The circuit plugs into the usual 110 volt AC receptacle through a plug 84. One contact of plug 84 is connected through a manual power on-off switch 86 and through a normally closed, manually reset, thermal overload switch 32 to PTC heating element 80. Switch 32 is constructed to open when the paraffin wax surrounding the heating section reaches a temperature of 146° C. This represents an overload temperature, and when switch 32 opens, it de-energizes the system, and this switch stays open until it is manually reset at the back panel 11 as shown in FIG. 1a. Manual power switch 86 is also located on the rear panel 11 shown in FIG. 1a. The other contact of plug 84 is directly connected to the other side of the PTC heating element 80. The manual power switch 86 is also connected through the normally closed thermal switch 32 and through the normally closed thermal switch 30 to one side of the PTC heating element 82, the other side of which is returned to the other contact of plug 84.

The thermal switch 30 is an automatic reset type, and it is constructed to open when the paraffin wax surrounding the heating section of the unit reaches a temperature of 130° C. and to close when the temperature of the wax falls to, for example, 125° C. A power-on indicator lamp 102 is located on the front panel of the unit (FIG. 1) and is connected through the switches 32 and 86 across the contacts of plug 84. Induction coil 44 is located in the cooling section 40, and this induction coil is connected across the contacts of switch 84 through the on/off switch 86. The induction coil 34 in the heating section is also connected across the contacts of plug 84 through the manually operated on/off switch 86.

When the unit is first turned on by closing the on/off switch 86, both PTC heating elements 80 and 82 are connected in parallel across the 110 volt AC source, and the heating section 16 of the unit rapidly heats up to operating temperature. When the wax reaches a temperature of 130° C.±1.5° C., switch 30 opens disconnecting the PTC 82, and leaving the PTC heating element 80 to maintain an operating temperature of, for example, 134° C. It is normal practice to keep the on/off switch 86 closed during the course of the day.

When the cold cartridge 50 is inserted into the heating section 16, the temperature of the wax drops, causing the thermal switch 30 to close so that the wax may be rapidly returned to its operating temperature heating the interior of the cartridge. Whenever the on/off switch 86 is closed, the indicator lamp 102 is energized indicating that the unit is operational.

When the cooling section 40 is at room temperature, the thermal switch 87 is open and the fan 46 is de-energized. However, when the hot cartridge is removed from the heating section 16 and inserted into the cooling section, its heat causes the thermal switch 87 to close and operate the fan. The fan continues to operate until the temperature of the cartridge within the cooling chamber is returned to room temperature, or until the cartridge has been removed and the interior of the cooling section returns to room temperature.

As described in U.S. Pat. No. 4,734,560 which issued to the present inventor on Mar. 29, 1988, the PTC heating element has been known for many years. The PTC heating element is composed of a semi-conductor ceramic, such as an appropriately doped barium titanate. This material has a positive thermal coefficient, and it has a property that at a certain temperature, known as the "Curie" point, its internal resistance suddenly increases if temperatures are raised above that point.

Accordingly, the PTC constitutes an attractive heating element because of its automatic temperature control. The PTC heating element is independent of voltage, and it can be used in connection with alternating current. Regardless of the voltage, the element will increase in temperature until the Curie point is reached, and at that point it will effectively cut off, serving inherently as an automatic temperature controller. Moreover, the PTC heating element does not require a protective relay in its circuit, because it is incapable of burning out. The Curie point of the PTC heating element can be set to any desired temperature level by controlling the doping of the ceramic material. In the case of the sterilizer unit of the present invention, the temperature level is set to a particular value, as will be described.

It is known that the Curie point in a PTC heating element cannot be set with any degree of accuracy, and variations up to±40% have been experienced from one PTC heating element to another. However, in the sterilizing unit of the present invention the PTC heating elements 80 and 82 are embedded in paraffin wax, as described above, and the wax is used to carry the heat from the heating elements to the interior of the heating section of the unit. The paraffin wax is selected to have melting point which corresponds with a high degree of accuracy to the desired temperature in the sterilizing unit. The Curie point of the PTC heating element 80 is then set to occur above the desired temperature, even with its widest variation. During normal operation the wax is usually not completely melted, and its latent heat establishes a precise sterilizing temperature for the unit. Accordingly, the sterilizing temperature may be set to be regulated to be within ±2° C., and to have a temperature reproducability of ±1.5° C.

Figure 9:
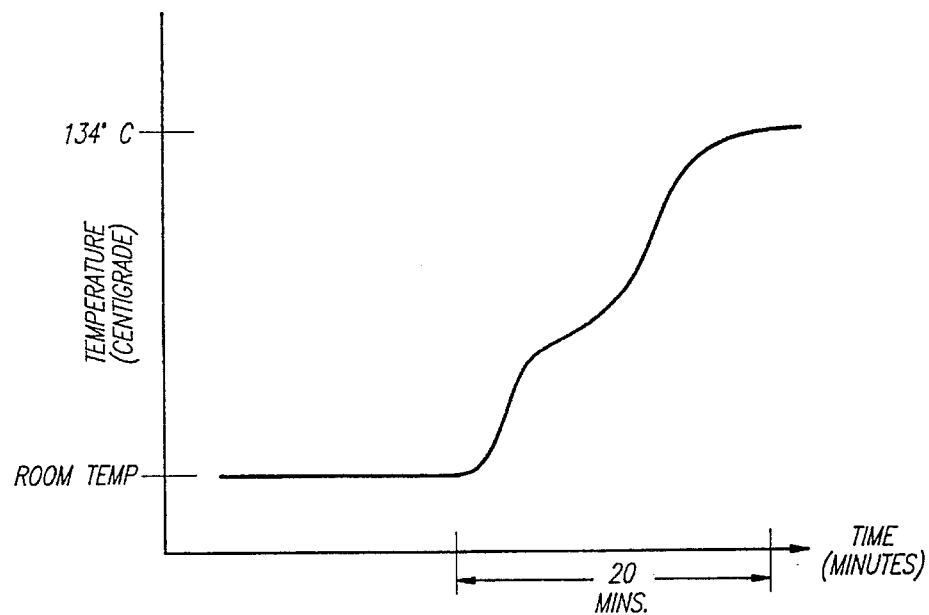
FIG. 9 is a curve showing the initial heat up in the heating section when the unit is first energized.
Figure 11:
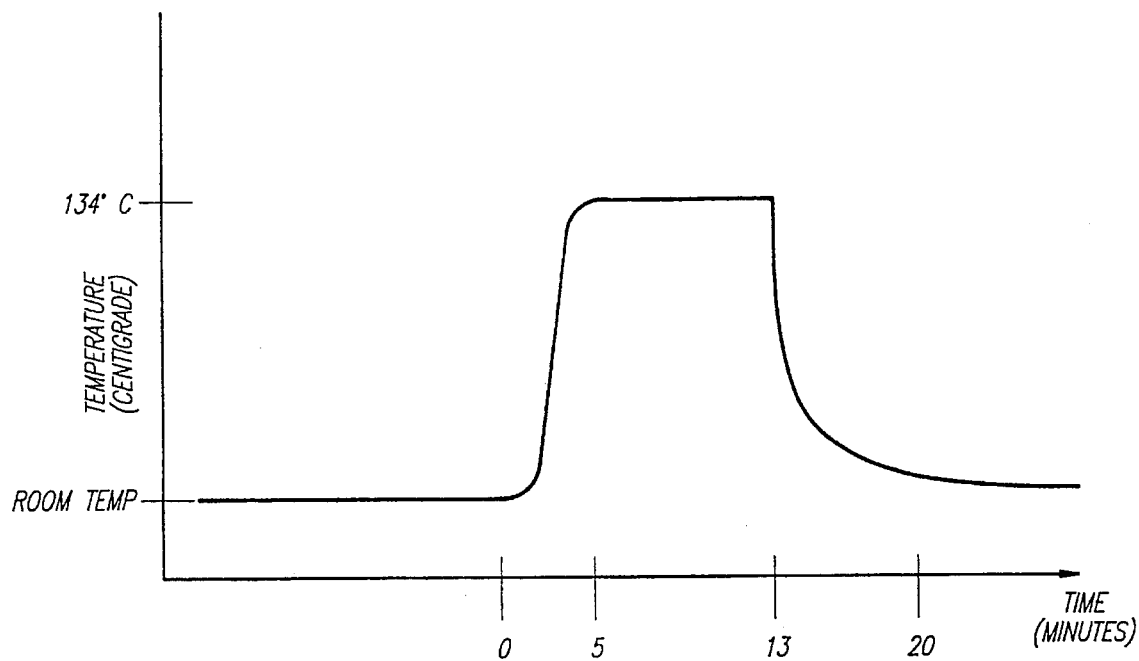
FIG. 11 is a curve showing the relation between temperature and time in the heating section of the sterilizing unit of FIG. 1.

The sterilizing unit in the embodiment being described has an added feature of rapid heat up of the heating section, as described above. Accordingly, when the sterilizer unit is first turned on, and is at room temperature, both heating elements 80 and 82 operate together rapidly to bring the paraffin wax up to a temperature of 130° C. When that temperature is reached, switch 30 opens and disconnects the PTC heating element 82 from the circuit. Then, the paraffin wax is maintained at an operating temperature of, for example, 134° C. by PTC heating element 80 which serves to help the operating temperature to within ±2°, as mentioned above. Accordingly, the temperature of the heating section follows the curve of FIG. 9 after the unit is first turned on, with the temperature being raised rapidly from room temperature to, for example, 134°, at which time the paraffin wax is maintained at a constant temperature by PTC heater element 80. Switch 32 is an overload switch and it stays closed through the sterilizing process, unless an overload condition occurs. Then switch 32 opens and must be reset manually.

To perform a sterilizing procedure the elements of the cartridge 50 shown in FIGS. 4 and 5 are assembled and placed in the cylindrical housing 52. Specifically, the adapter 56 is screwed on to the end of handpiece 54 and the combined handpiece and adapter are fitted into friction fit into a channel in the insert 58. The insert 58 and attached handpiece 54 are then inserted into the cylindrical housing 52. The water ampoule 60 is inserted into the other end of insert 58. The cap 62 is then placed over the insert 54 and screwed onto the end of the cylindrical housing 52. When that occurs, a barb 100 in the insert 58 pierces the water ampoule 60 so that water from the ampoule can flow down through the insert and through the internal pipes of the handpiece 54.

The water-containing ampoule 60 is formed, for example, of polystyrene, and it becomes gradually flattened by heat during the heating cycle so that water in the ampoule is slowly dispensed to flush the handpiece and then to be converted to steam. The dispensing of the water from the ampoule continues until it becomes completely flattened. When the cartridge 50 is placed in the heating unit, the water from the ampoule is converted to steam. The geometry of the cartridge assures a homogeneous mixture of air and steam. When the cartridge is placed in the accurately temperature-controlled heating section of the sterilizing unit, the conversion of water to steam produces a corresponding pressure that follows a conventional vaporization of water table. Such a relationship of temperature verses steam pressure correlated to time is universally accepted as the condition which causes sterilization, that is:

121° C. at 20 PSI for 20 minutes
128° C. at 30 PSI for 10 minutes
134° C. at 35 PSI for 3.5 minutes Accurate control of the temperature within the cartridge is necessary to prevent rupture of the cartridge or damage to the instruments being sterilized.

Accordingly, the water ampoule 60 is placed in the enclosed cartridge in such a manner as to force water, water vapor and steam through the tubing and channels of the handpiece to flush debris and biological contaminants from the instrument. The flushing process also insures contact with the steam to sterilize the internal parts of the handpiece as it is being sterilized.

The water in the water ampoule 60 is previously processed by ion exchange, distillation or reverse osmosis or a combination of all three. Such water also performs a descaling operation of the instruments being sterilized. Attached to the top of the ampoule is a color-change indicator-integrator which serves to indicate that sufficient temperature, pressure and time has elapsed to insure sterilization. At the end of the sterilization process, and when the cartridge is disassembled, the indicator on the flattened ampoule will indicate whether or not the instrument has been properly sterilized. The indicator may be of the type commercially manufactured and marketed by Albert Brown Ltd. of Leicester, United Kingdom. The color dot which forms the indicator has a particular color at the beginning of the process, and it assumes a selected color only when the process has been completed and the necessary time, steam and temperature criteria have been achieved.

Other liquids may be contained in the ampoule, such as, a lubricant which additionally serves to lubricate the handpiece; or disinfecting chemicals, such as alcohol, formaldehyde, and the like, which permit reductions in the sterilization times and temperatures.

The circuitry in the cap 62 assures that the sterilization cycle in the heating section of the unit will have a proper time duration, this being achieved by a pressure switch 90 which measures the pressure in the cartridge 50 to control the time function, this being a more accurate basis than attempting to measure temperature directly.

Figure 7:
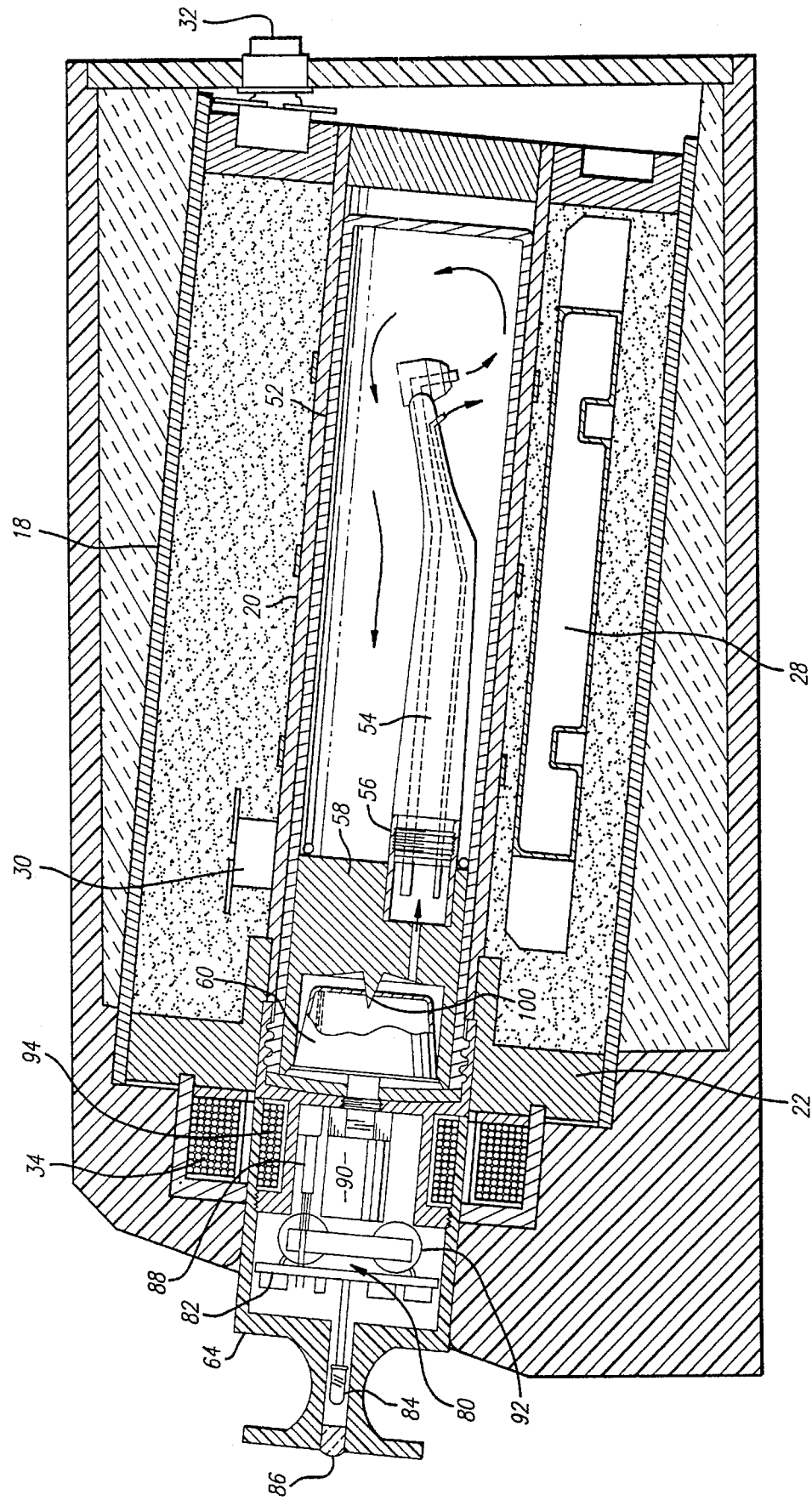
FIG. 7 is a side sectional view of the elongated cartridge of FIG. 6 inserted into the heating section of the sterilizing unit of FIG. 1.
Figure 10:
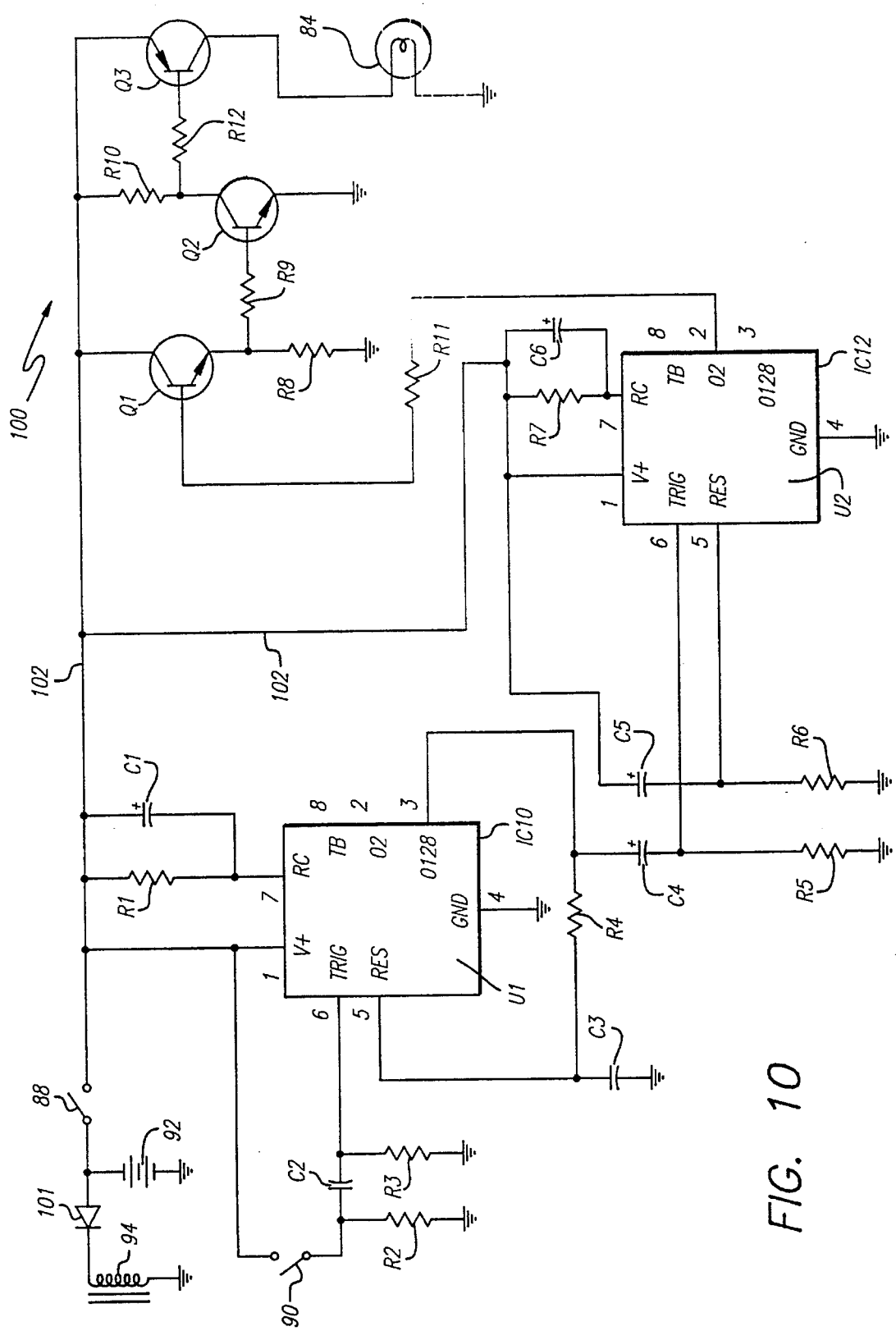
FIG. 10 is a circuit diagram of a timing circuit which is included in the elongated cartridge of FIGS. 4, 5 and 6.

The timing/logic control module 80, as shown in FIG. 7, is contained in cap 62. The module includes a printed circuit board 82 on which the electrical elements of FIG. 10 are mounted. The printed circuit board also mounts an indicator lamp 84, which, when energized illuminates a lens 86 in cover 64 (FIG. 4). The printed circuit board 82 also mounts a thermal switch 88. The pressure switch 90 is also connected to the circuit in module 80, as are one or more chargeable batteries 92.

An induction coil 94 is mounted on cartridge 50 around the module 80, and this coil is inductively coupled to induction coil 34 when the cartridge is inserted into the heating section 16 (FIG. 2), and to induction coil 44 (FIG. 3) when the cartridge is inserted into the cooling section.

As shown in FIG. 8, induction coil 94 is connected to a charger for battery 92. Accordingly, the charger is energized whenever the cartridge is inserted into the heating section, and the charger is also energized whenever the cartridge is inserted into the cooling section. This is assures that the batteries are maintained in a charged condition as the unit is used. As mentioned above, fan 46 (FIG. 8) is also energized whenever the cartridge is inserted into the cooling section.

The electrical circuitry for the timing logic control module 80 of FIG. 7 is shown in FIG. 10.

The electrical circuitry of FIG. 10 includes two integrated circuits IC10 and IC12. Each of the integrated circuits is of the type designated 7242. The Q2 output terminal of integrated circuit IC12 is connected to a buffer amplifier 100 which is made up of two NPN transistors Q1 and Q2 of the type designated 2N3904, and a PNP transistor Q3 of the type designated PN2907. The collector of the transistor Q3 is connected to one terminal of the indicator lamp 84 of FIG. 7, the other terminal of the indicator lamp being grounded. The temperature switch 88 of FIG. 7 is connected to a common lead 102 and to the positive terminal of battery 92, the negative terminal of the battery being grounded.

When the cartridge 50 of FIG. 6 is inserted into the heating section 12 (FIG. 2) the cartridge begins to heat up. When a particular temperature is reached within the cap 62 of the cartridge, the temperature switch 88 closes. The circuit of FIG. 10 is now energized and indicator lamp 84 is illuminated and is visible through the cover 64 of the cartridge. It will be appreciated that the circuit of FIG. 10 will not be energized until not only the internal temperature of the cartridge reaches a predetermined temperature but the temperature of all hand pieces, or other instruments, which may be supported within the cartridge, also reaches the predetermined temperature.

Integrated circuit IC10 is connected as a timer. However, the timing interval of the timer is not initiated until the pressure within the cartridge 50 reaches a predetermined pressure of, for example, 26 PSI. This pressure corresponds to the actual sterilizing temperature of the instruments within the cartridge, and it is an extremely accurate measurement of the sterilizing temperature.

Accordingly, the circuit of FIG. 10 is activated to begin timing only after all the instruments within the cartridge reach a predetermined sterilizing temperature. At that time, the pressure switch 90 opens, and the integrated circuit IC10 begins its timing function. In the embodiment under consideration, the time interval is set to ten minutes. Until the end of the timing interval is reached, the indicator lamp 84 is continuously energized.

When the end of the timing interval is reached, the output Q128 of the timer integrated circuit IC10 changes state and triggers the integrated circuit IC12 so that the indicator lamp 84 is caused to flash. At that time, the timer integrated circuit IC10 sets itself to be ready for the next operation. As mentioned above, the buffer amplifier 100 provides sufficient energy to energize the indicator lamp 84 in its continuous or flashing state.

As also shown in FIG. 10 battery 92 is connected through a diode 101 to induction coil 94. As shown in FIG. 8, when the cartridge 50 is inserted into the heating or cooling section of the unit 10, alternating current in induction coil 34 or 44 induces a charging current in induction coil 94 to provide a charging current for battery 92 and an instantaneous energizing potential for the electronic circuitry of FIG. 10 in the event that battery 92 has not attained its fully charged condition. Accordingly, battery 92 is maintained in a fully charged condition when the cartridge is in either the heating section or the cooling section of the unit.

To sum up, when the cartridge 50 is inserted, for example, in the heating section 16 of the unit, it is heated to the selected operating temperature. When the cartridge reaches that operating temperature, temperature switch 88 closes and indicator lamp 84 is illuminated. The heating of the interior of the cartridge continues until the internal pressure reaches 26 PSI which, this being an accurate designation that the interior of the cartridge and the instruments contained therein have now reached sterilizing temperature. When that pressure is reached, pressure switch 90 opens and the integrated circuit IC10 begins its timing function. After ten minutes, the timer formed by integrated circuit IC10, times out and causes integrated circuit IC12 to send a flashing signal to the indicator lamp 84. The operator then removes the cartridge 50 from the heating section 16 and places it in the cooling section 40. The heating section of the sterilization unit 10 is now ready to receive another cartridge. The indicator lamp 84 continues to flash until the pressure within the cartridge contained in the cooling section, drops, for example, to 19 PSI. Then pressure switch 90 closes, and the timer integrated circuit IC10 resets itself and the indicator lamp 84 returns to its continuously energized condition. The original is left in the cooling section 40 until the internal temperature returns to room temperature, at which time temperature switch 88 opens, and the indicator lamp 84 is extinguished, so that the cartridge may be now removed from the cooling section. It should be noted that if during any operation pressure within the cartridge is lost, the pressure switch 90 will immediately close and discontinue the operation and extinguish the indicator lamp 84.

To reiterate, the sterilization unit of the invention responds to internal pressure of the cartridge 50 of, for example, 26 PSI, which is a precise measurement of the actual temperature of the instruments being sterilized. The timing cycle begins only after all instruments reached the predetermined sterilizing temperature, at which time the internal pressure reaches 26 PSI, and the timing cycle begins. Accordingly, the unit of the invention is not only precise in its measurement of the sterilizing temperature through pressure, but it also adjusts itself automatically to load conditions, that is, to the size of the instruments, and to the number of the instruments within the cartridge. All the instruments within the cartridge must reach sterilizing temperature, before the pressure will rise sufficiently to start the timing cycle.

The invention provides therefore a relatively inexpensive unit for sterilizing dental handpieces, and the like, which is simple to operate, which requires minimum sterilization time, and which will not harm or dull the instruments being sterilized. A lubricant may be added to the liquid in the ampoule to lubricate the instruments, and/or disinfectants may be added. The entire process takes place in a sealed cartridge and the instruments are not removed until the sterilization process has been completed. There is no venting to the atmosphere of any contaminating gases; and the instruments in the cartridge, after sterilization, cool down without contamination.

It will be appreciated that while a particular embodiment of the of sterilization system of the present invention has been shown and described, modifications may be made. It is intended in the following claims to cover all modifications which come within the true spirit and scope of the invention.

I claim:

1. A sterilization unit for dental handpieces, and other surgical instruments, comprising; an elongated cartridge for removably containing a dental handpiece, or other instruments to be sterilized; a housing defining a heating section and a cooling section disposed adjacent to one another and heat insulated from one another and having first and second apertures for respectively receiving the cartridge successively into the heating section during a sterilizing cycle and into the cooling section during a cooling cycle; said heating section including inner and outer elongated tubular cases mounted in coaxial relationship with one another and radially displaced from one another to form an annular chamber therebetween, and said inner case forming a heat chamber; a quantity of thermal conductive material filling said annular chamber and hermetically sealed therein; heating means mounted in said annular chamber and submerged in said thermal conductive material, and said cooling section including means including a tubular cooling tube for receiving the cartridge after the cartridge has been removed from the heating section and for transferring heat from the cartridge through the housing to the external atmosphere.

2. The unit defined in claim 1 in which said thermally conductive material is paraffin wax.

3. The unit defined in claim 2, in which said heating means is electrically energized, and includes at least one Positive Temperature Coefficient (PTC) heating element.

4. The unit defined in claim 2, in which said heating means is electrically energized and comprises a pair of Positive Temperature Coefficient (PTC) heating elements, and which unit further includes thermally responsive switching means immersed in said paraffin wax for connecting said heating elements in parallel until the paraffin wax reaches a predetermined temperature and then for disconnecting one of said heating elements.

5. The unit defined in claim 1, in which said heat transferring means in said cooling section includes an electric fan, and circuitry including a thermal switch for energizing said fan when said cartridge is inserted into said cooling section in a heated condition above a particular temperature and to de-energize said fan when said cartridge is cooled below said particular temperature.

6. A sterilization unit for dental handpieces, and other surgical instruments, comprising: an elongated cartridge for removably containing a dental handpiece, or other instruments to be sterilized; a housing defining a heating section and having an aperture for receiving the cartridge into the heating section; said heating section including inner and outer tubular cases mounted in coaxial relationship with one another and radially displaced from one another to form an annular chamber therebetween, and said inner case forming a heat chamber; a quantity of thermal conductive material filling said annular chamber and hermetically sealed therein; and heating means mounted in said annular chamber and submerged in said thermal conductive material, in which said cartridge includes an elongated heat-conductive cylindrical housing having an open end and a closed end for receiving a dental handpiece, or other instrument, through the open end; a tubular insert having an outer diameter less than the inner diameter of the cylindrical housing also received through the open end of the cylindrical housing and forming a mount for the handpiece; and a container for liquid mounted coaxially within the insert for supplying a liquid to the interior of the housing to be vaporized therein, said insert including an aperture communicating with the interior of the handpiece for supplying the liquid to the interior of the handpiece to be vaporized therein.

7. The unit defined in claim 6, in which the cartridge includes an electric module mounted therein which includes timing circuitry for automatically initiating a sterilizing cycle of a predetermined time interval after the instrument in the cylindrical housing reaches a predetermined sterilizing temperature.

8. The unit defined in claim 7, in which the cartridge includes a cap member forming a mount for said electric module, said cap member being mounted on said cylindrical housing at the open end thereof and in coaxial relationship therewith to close and seal the interior of the cylindrical housing.

9. The unit defined in claim 8, in which the cartridge includes a cover for said electric module threadably mounted on said cap member and shaped to define a handle for inserting the cartridge into the heating section and for withdrawing the cartridge from the heating section.

10. The unit defined in claim 9, in which said electric module included in the cartridge includes an indicator lamp visible through the end of said cover.

11. The unit defined in claim 7, in which said circuitry in said electric module includes a pressure switch for initiating said sterilizing cycle when the internal pressure in said cylindrical housing reaches a predetermined value.

12. The unit defined in claim 7, and which includes a first induction coil mounted in said housing and surrounding said aperture and adapted to be connected to a source of electric energy, a second induction coil mounted on said cartridge to be inductively coupled with said first induction coil when the cartridge is inserted into the heating section, at least one rechargeable battery mounted on said module for energizing electric circuitry in said module, and a charging circuit for said battery connected to said second induction coil.

13. The unit defined in claim 6, in which said liquid container included in the cartridge is in the form of a collapsible ampoule, and in which said insert includes projecting means for piercing the liquid ampoule, said liquid ampoule collapsing in response to heat in said cylindrical housing to force liquid from the ampoule through the insert into the interior of said cylindrical housing and into the interior of the handpiece to be vaporized therein, to sterilize internal components of the handpiece and to flush debris and diological contaminants from the interior of the handpiece.

14. The unit defined in claim 13, in which the cartridge includes a color change indicator means mounted on said ampoule to assure that sufficient temperature and pressure has occurred and sufficient time has elapsed to insure correct sterilization.

15. The unit defined in claim 6, in which the liquid in the liquid container included in the cartridge is mineral-free water processed by at least one of the following procedures: ion exchange, reverse osmosis, and distillation.

16. The unit defined in claim 6, in which said liquid container included in the cartridge contains a lubricant.

17. The unit defined in claim 6, in which the liquid container contains a disinfectant.

* * * * *